United States Patent [19]

Kolts

[11] Patent Number: 4,621,163

[45] Date of Patent: Nov. 4, 1986

[54] CONVERSION OF $C_3$ AND $C_4$ HYDROCARBONS TO LESS SATURATED HYDROCARBONS

[75] Inventor: John H. Kolts, Ochelata, Okla.

[73] Assignee: Phillips Petroleum Company, Bartlesville, Okla.

[21] Appl. No.: 758,939

[22] Filed: Jul. 25, 1985

[51] Int. Cl.$^4$ .................................................. C07C 4/02
[52] U.S. Cl. .................................... 585/653; 585/651; 585/661
[58] Field of Search .................... 585/651, 653, 661

[56] References Cited

U.S. PATENT DOCUMENTS

| | | | |
|---|---|---|---|
| 2,415,477 | 2/1947 | Folkins et al. | 585/651 |
| 3,644,557 | 2/1972 | Senes et al. | 585/651 |
| 3,751,514 | 8/1973 | Hoppstock et al. | 585/653 |
| 3,751,516 | 8/1973 | Frech et al. | 585/653 |
| 3,766,278 | 10/1973 | Bogart et al. | 585/651 |
| 4,087,350 | 5/1978 | Kolombos et al. | 585/653 |
| 4,093,536 | 6/1978 | Heckelsberg | 585/653 |
| 4,152,300 | 5/1979 | Riesser | 502/324 |
| 4,159,970 | 7/1979 | Heckelsberg | 502/324 |
| 4,471,151 | 9/1984 | Kolts | 585/651 |

FOREIGN PATENT DOCUMENTS

| | | | |
|---|---|---|---|
| 47-42703 | 12/1972 | Japan | 585/653 |
| 1306087 | 2/1973 | United Kingdom | 585/651 |
| 0422165 | 8/1974 | U.S.S.R. | 585/651 |
| 0626111 | 9/1978 | U.S.S.R. | 585/651 |

*Primary Examiner*—John Doll
*Assistant Examiner*—Lance Johnson
*Attorney, Agent, or Firm*—Charles F. Steininger

[57] ABSTRACT

A method for the conversion of $C_3$ and $C_4$ hydrocarbons to less saturated hydrocarbons, such as ethylene and propylene and particularly ethylene, includes contacting the feed hydrocarbons with mixed oxides comprising a major proportion of magnesium and a minor proportion of manganese, preferably under conditions which selectively convert the feed hydrocarbons to ethylene and ethane and particularly ethylene, including a temperature between about 625° C. and 850° C. The method is preferably carried out in the presence of steam at a mole ratio of steam/hydrocarbon of less than about 10:1. Selectivity to ethylene and ethane and particularly ethylene is improved and the life of the catalyst, during which the desired selectivity is attained, is extended by adding a promoting amount of at least one oxide of calcium, barium, strontium, tin and antimony. Further improvement can be obtained by limiting the amount of bound or fixed sulfur in the catalyst.

19 Claims, No Drawings

CONVERSION OF $C_3$ AND $C_4$ HYDROCARBONS TO LESS SATURATED HYDROCARBONS

The present invention relates to a conversion of $C_3$ and $C_4$ hydrocarbons to less saturated hydrocarbons. In a more specific aspect, the present invention relates to a method for the conversion of $C_3$ and $C_4$ alkanes to less saturated hydrocarbons, particularly ethylene and propylene and preferably ethylene.

BACKGROUND OF THE INVENTION

Olefins, such as ethylene and propylene, have become major feedstocks in the organic chemical and petrochemical industries. Of these, ethylene is by far the most important chemical feedstock since the requirements for ethylene feedstocks are about double those for propylene feedstocks. Consequently, improved methods for the conversion of less valuable hydrocarbons to ethylene and propylene and particularly to ethylene are highly desirable.

Numerous suggestions have been made for the production of ethylene and propylene, particularly ethylene, from various feedstocks by a wide variety of processes.

At the present time ethylene is produced almost exclusively by dehydrogenation or thermal cracking of ethane and propane, naptha and, in some instances, gas oils. About 75% of the ethylene currently produced in the United States is produced by steam cracking of higher normally gaseous hydrocarbon components of natural gas, since natural gas contains from about 5 volume % to about 60 volume % of hydrocarbons other than methane. However, in most instances, the content of ethane and higher normally gaseous hydrocarbons in natural gas is less than about 25% and usually less than about 15%. Consequently, these limited quantities of feedstocks, which are available for the production of ethylene and propylene and particularly ethylene, must be utilized efficiently. Unfortunately, these processes result in low conversions to olefins and selectivity to ethylene, as opposed to propylene, is poor. In addition, relatively severe conditions, particularly temperatures in excess of about 1000° C., are required and such processes are highly energy intensive.

In order to reduce the severity of the conditions and, more importantly, to improve the conversion of normally gaseous feedstocks, to ethylene and propylene, and the selectivity to ethylene, numerous processes involving the use of solid contact materials have been proposed. Some of these proposals utilize inert solid contact materials to improve contact between the feed hydrocarbons and steam and also to maintain a more even temperature throughout the zone of reaction. In other instances, the solid contact material is catalytic in nature. Such use of solid contact materials, particularly catalysts, have resulted in modest improvements in conversion to ethylene and propylene but the selectivity to ethylene is improved very little. It is, therefore, highly desirable that improved catalytic processes be developed, particularly processes which increase the selectivity to ethylene, as opposed to propylene. However, little is understood concerning the manner in which such catalysts function, why certain components are effective while similar components are ineffective or why certain combinations of components are effective and other combinations are not. Obviously, a number of theories have been proposed by workers in the art, but this only adds to the confusion, since it appears that each theory explains why a particular catalytic material works well but does not explain why similar catalytic materials do not work and why other dissimilar materials are effective. As a result, the art of catalytic conversion of hydrocarbons to olefins remains highly unpredictable.

SUMMARY OF THE INVENTION

It is therefore an object of the present invention to provide an improved method for the conversion of $C_3$ and $C_4$ feed hydrocarbons to less saturated hydrocarbons, which overcomes the above and other disadvantages of the prior art. Still another object of the present invention is to provide an improved method for the catalytic conversion of $C_3$ and $C_4$ hydrocarbons to less saturated hydrocarbons, particularly ethylene and propylene. Yet another object of the present invention is to provide an improved method for the conversion of $C_3$ and $C_4$ hydrocarbons to ethylene and propylene, in which the selectivity to ethylene is significantly improved. These and other objects of the present invention will be apparent from the following description.

In accordance with the present invention, $C_3$ and $C_4$ hydrocarbons, particularly propane and butanes, are converted to less saturated hydrocarbons, particularly ethylene and propylene with a high selectivity to ethylene, by contacting the feed hydrocarbons with a contact material comprising a major portion of an oxide of magnesium and a minor portion of an oxide of manganese, under conditions sufficient to convert the feed hydrocarbons to the less saturated product hydrocarbons. Minor amounts of at least one oxide of at least one metal selected from the group consisting of calcium, barium, strontium, tin and antimony have been found to extend the effective life of the catalyst. In addition, mixing steam with the feed hydrocarbon has also been found to extend the effective life of the catalytic material. The effectiveness of the catalyst is also improved by limiting the sulfur content thereof.

DETAILED DESCRIPTION OF THE INVENTION

The hydrocarbon feed, in accordance with the present invention, can include any normally gaseous hydrocarbon stream containing significant amounts of $C_3$ and $C_4$ hydrocarbons, particularly propane and n-butane, with n-butane being preferred. The presence of other normally gaseous components or even normally liquid components, which vaporize at operating conditions, are not detrimental to the process. For example, it has been found that when isobutane is utilized, in accordance with the present invention, the catalyst of the present invention shifts the product stream from isobutene to propylene and, therefore, one of the desired products of the present invention is produced. On the other hand, it has been found that the catalytic process of the present invention is ineffective, as compared with a strictly thermal process, in improving the conversion of ethane to ethylene. However, the presence of ethane in the feed hydrocarbons, obviously, is not detrimental. Components other than hydrocarbons are also not detrimental. The primary criteria in all cases is the cost or difficulty of separating inert materials or the products of components other than $C_3$ and $C_4$ hydrocarbons from the desired ethylene and propylene and whether such separation is less costly and/or less difficult before or after conduct of the process of the present invention.

Suitable feedstocks for the process of the present invention can be obtained from any source, including natural gas, refinery off-gases and the like. However, the most convenient and abundant source is $C_3$ and $C_4$ hydrocarbon streams recovered during the processing of a natural gas to produce a pipeline gas for heating purposes. Conventionally, $C_2$ and higher hydrocarbons are separated from methane to produce a pipeline gas for heating purposes, which predominates in methane, by compression and expansion, cryogenic means or a combination of both. Usually, the natural gas, either at a high pressure as produced or compressed to a high pressure, is treated to successively condense first normally liquid hydrocarbons ($C_6+$ hydrocarbons or natural gasoline), then $C_5$, followed by $C_4$, then $C_3$ and finally, $C_2$ hydrocarbons, by cooling to successively lower temperatures with the separation or fractionation of the condensed liquid from uncondensed vapor between cooling stages. Thus, individual streams predominating in an individual hydrocarbon, such as $C_4$, $C_3$ and $C_2$, can be obtained or streams predominating in combinations of the individual hydrocarbons can be recovered. Accordingly, the thus separated propane stream or thus separated butanes stream can be utilized as a feed hydrocarbon for the present invention or a stream predominating in a mixture of propane and butanes can be utilized. Obviously, the latter would eliminate the necessity of one stage of cooling and separation in a natural gas processing system.

The catalytic material of the present invention comprises a major portion of at least one oxide of magnesium and a minor portion of at least one oxide of manganese. The magnesium oxide is referred to herein, from time to time, as the base material and the manganese oxide as the promoting or active material as a matter of convenience, simply because the magnesium oxide is the major component and the manganese oxide is the minor component, rather than by way of categorizing the components. As will appear hereinafter, both components are necessary and both are catalytically active in the process. In any event, manganese oxide is present in the mixture in amounts from about 0.1 to about 30% by weight, expressed in terms of metallic manganese based on the total weight of the catalytic mixture. Preferred manganese contents are between about 0.5 and about 10% of metallic manganese, based on the total weight of the mixture.

The method of catalyst preparation does not appear to be critical, so long as the desired final composition of the component metal oxides is obtained. Suitable methods of preparation include slurry blending, solution blending, dry blending, impregnation and co-precipitation, all of which are well known to those skilled in the art. A convenient method is to add metal solids such as MgO or Mg(OH)$_2$ to a blending apparatus along with an aqueous solution of the manganese metal salt [for example Mn(NO$_3$)$_2$] and mixing for several minutes, for example, 2 to 15 minutes, to form a thick slurry. In the interest of economy, excess water should be avoided. Additional catalyst components or promoters, hereafter referred to, may also be added as desired, either as solids or solutions before or during blending. The resulting slurry is then dried in air by conventional means, at about 100° C. to 150° C., calcined for about four hours, at about 750° C. to 800° C., and then ground, sieved and, optionally, pelleted or otherwise sized by means well known in the art. The additional promoters can also be added by impregnating the same on the preformed Mn/Mg.

The process of the present invention can be carried out in fixed, moving, fluidized, ebulating or entrained bed reactors. For experimental purposes and, obviously, to permit accurate measurement and precise control of the process variables, the runs hereinafter set forth in the examples were conducted in a fixed bed reactor.

During operation, in accordance with the present invention, it has been found that small amounts of the feedstock are converted to coke, which is then deposited upon the catalyst and contributes to a decline in the catalyst activity, particularly the selectivity to ethylene. Accordingly, it is desirable to periodically regenerate the catalyst by conventional techniques of carbon removal, such as treatment with an oxygen-containing gas, such as air. During such regeneration, it may also be desirable to use inert gas or steam dilution to control burn-off temperatures, as is also well known to those skilled in the art.

It has also been discovered, in accordance with the present invention, as will be shown by the examples hereinafter, that the addition of steam to the feed hydrocarbon significantly extends the effective life of the catalyst between regenerations.

Following preparation of the catalyst, the catalyst may be prepared for use by purging with an inert gas, such as nitrogen. Normally, the catalyst would be disposed in the reactor and brought up to reaction temperature by preheating with air, then purging with hot nitrogen and, finally, introducing the hydrocarbon feed. Since it is preferred that steam be added to the hydrocarbon feed, in the conduct of the process of the present invention, it may be preferred to use steam rather than nitrogen as a purging gas. The catalyst may also, optionally, be pretreated with hydrogen before use. Such treatment is preferably carried out at about the operating temperature of the process and at a pressure up to about 600 psia. Such hydrogen pretreatment appears to reduce higher oxidation states of manganese and, thereby, reduce initial carbon oxide formation.

With the exception of the temperature of operation, the operating conditions of the process, in accordance with the present invention, do not appear to be highly critical. Accordingly, the following conditions of operation are those found effective and preferred:

The steam/hydrocarbon mole ratio may be between 0 and about 10/1 and is preferably about 0.5/1 to about 5/1.

The hydrocarbon gas hourly space velocity (GHSV) may range from about 100 to about 3000 but is preferably between about 500 and about 1000.

Operating pressure may be between about 0.1 and about 100 psia and is preferably between about 1 and about 60.

The temperature of operation appears to be significant in the conversion of feed hydrocarbons to olefins and, particularly, in improving the selectivity to ethylene. Suitable temperatures range between about 625° C. and about 850° C. with the preferred range being between about 650° C. and about 775° C.

The nature and the advantages of the present invention are illustrated by the following examples.

In the runs of the examples the catalysts were evaluated by using either a 6 mm quartz reactor containing 5 cc of catalyst or an 18 mm quartz reactor containing 25 cc of catalyst. Snap samples of reactor effluent were analyzed by gas chromatography. Typically, a bed of catalyst was pretreated by air oxidation for 10 minutes, nitrogen purged for two minutes, hydrogen treated for 10 minutes and, finally, nitrogen purged. The catalyst bed was brought up to reactor temperature before beginning the flow of feed hydrocarbon. The feed hydrocarbon was passed through a water saturator at 81° F. to provide a steam/hydrocarbon molar ratio of approximately 1/1. The flow rate was adjusted to provide a one second residence time through the catalyst bed.

EXAMPLE 1

A first series of runs was made utilizing a manganese oxide/magnesium oxide catalyst for the conversion of n-butane feed at a 1/1 steam/hydrocarbon ratio. For comparative purposes, all runs were made at a constant 50% feed conversion (mole % of n-butane converted). Consequently, the temperatures reported are the temperatures necessary to attain a constant 50% feed conversion. The selectivities are also based on mole % of n-butane converted to a particular product. In the series of runs referred to, varying amounts of manganese oxide were utilized, with the manganese content being expressed as wt. % of elemental manganese based on the total weight of the mixture of manganese oxide and magnesium oxide. Comparison was made with quartz chips, as opposed to the catalytic oxide mixture, thus representing a comparison with a thermal or non-catalytic steam cracking operation. Additional minor products included methane and lesser amounts of butenes, butadiene, propane and carbon oxides, but are not reported.

TABLE 1

| Catalyst | Bed Temp., °C. | Selectivity $C_2^=$ | $C_3^=$ | $C_2$ | $\frac{C_2^= + C_2}{C_3^=}$ |
|---|---|---|---|---|---|
| 1%. Mn/MgO* | 678 | 36 | 30 | 15 | 1.70 |
| 2%. Mn/MgO | 668 | 35 | 30 | 16 | 1.70 |
| 4% Mn/MgO | 659 | 35 | 27 | 19 | 2.00 |
| 6% Mn/MgO | 654 | 33 | 27 | 20 | 1.96 |
| 8% Mn/MgO | 647 | 33 | 26 | 21 | 2.08 |
| Quartz Chips** | 720 | 30 | 39 | 7 | 0.95 |

*Although the catalysts are mixtures of the oxides of Mn and Mg, the Mn is reported as the wt % of the element since its oxide composition varies with the state of reduction.
**Non-catalytic quartz chips were used in a control run to determine product distribution for non-catalytic steam cracking.

A review of the data of Table 1 makes it clear that the manganese oxide/magnesium oxide catalyst substantially increased the selectivity to ethylene and the selectivity to total $C_2$'s over propylene, when compared with the non-catalytic run with quartz chips. It should also be noted that the non-catalytic run required a much higher temperature in order to obtain the same conversion of n-butane. A further observation, which can be made, is that, as the content of manganese oxide was increased, the reaction temperature for 50% n-butane conversion decreased.

As was previously pointed out, both components of the manganese oxide/magnesium oxide catalyst are necessary. This is illustrated by the following example.

EXAMPLE 2

In this series of tests a manganese oxide/magnesium oxide catalyst was compared with manganese oxide alone and quartz chips (thermal) for the conversion of n-butane. 25 cc or 30.9 grams of manganese oxide/magnesium oxide catalyst containing 3.5 wt. % manganese, expressed in terms of elemental manganese based on the total weight of the catalyst, was disposed in the reactor. N-butane was passed through the catalyst bed at a rate of 100 cc/min and steam at a rate of 100 cc/min. The catalyst was regenerated at intervals of about 10 minutes by passing 100 cc/min of air therethrough. Samples were taken 2 minutes after hydrocarbon feed and steam were started. Pressure over the catalyst bed was maintained between about 4 and 5 psig. The other conditions of operation were the same as those utilized in Example 1. The runs with magnesium oxide and quartz were conducted in the same manner.

TABLE 2

| Bed Temp., °C. | Conv. | $C_2^=$ | $C_3^=$ | $C_2$ | $C_3$ | $C_4^= + C_4^= =$ | $CH_4$ | $CO_x$ |
|---|---|---|---|---|---|---|---|---|
| 672 | 45.5 | 34.2 | 27.6 | 17.3 | 0.5 | 3.9 | 13.4 | 3.0 |
| 699 | 52.8 | 38.1 | 26.7 | 14.0 | 0.5 | 2.5 | 15.3 | 2.9 |
| 724 | 67.9 | 39.3 | 23.3 | 13.0 | 0.5 | 2.0 | 18.0 | 3.8 |
| MgO only (25 cc/17.7 grams) | | | | | | | | |
| 673 | 32.5 | 26.3 | 43.3 | 7.8 | 0.6 | 3.4 | 18.1 | 0.5 |
| 697 | 52.5 | 27.8 | 40.8 | 7.5 | 0.7 | 3.4 | 19.0 | 0.7 |
| 723 | 68.4 | 31.0 | 36.5 | 6.9 | 0.7 | 3.8 | 20.2 | 0.7 |
| Quartz chips | | | | | | | | |
| 675 | 23.3 | 26.5 | 44.3 | 7.5 | 1.0 | 3.1 | 17.6 | — |
| 700 | 38.5 | 29.3 | 41.4 | 6.7 | 0.7 | 3.8 | 18.0 | — |
| 726 | 57.3 | 32.4 | 37.4 | 6.4 | 0.6 | 4.4 | 18.7 | — |

It is to be observed from the above Table that substantially increased selectivity to $C_2$'s, and particularly to ethylene, is obtained when utilizing the manganese oxide/magnesium oxide catalyst of the present invention as opposed to magnesium oxide only or quartz chips. As a matter of fact, it can be seen that there is no observable difference between the strictly thermal conversion with quartz chips and that obtained utilizing magnesium oxide alone.

In certain prior art references, it has been suggested that $C_6+$ hydrocarbons can be cracked and/or dehydrogenated by treatment with manganese oxide and/or rhenium oxide and a Group IIA metal or mixtures thereof. However, it has been found, in accordance with the present invention, that rhenium oxide is not the equivalent of manganese oxide in the process of the present invention and that Group IIA metal oxides, other than magnesium oxide, are not effective bases for the catalyst combinations of the present invention.

The following example is illustrative. In this series of tests typical conditions were 25 cc of 16–40 mesh contact material, n-butane feed hydrocarbon at 480 GHSV and a steam/hydrocarbon ratio of 1/1. Other operating conditions and the mode of operation were the same as in the previous examples. The results of these comparisons are shown in the following table.

TABLE 3

| Catalyst | Bed Temp., °C. | Conv | Selectivity $C_2^=$ | $C_3^=$ | $C_2$ | $\frac{C_2^= + C_2}{C_3^=}$ |
|---|---|---|---|---|---|---|
| Quartz chips | 720 | 50 | 30 | 39 | 7 | 0.95 |
| 4% Mn/MgO | 659 | 50 | 35 | 27 | 19 | 2.00 |
| 5% Re/MgO | 668 | 50 | 4 | 6 | 6 | 1.67 |
| 5% Mn/CaO | 718 | 50 | 32 | 32 | 11 | 1.43 |

It is to be observed from the above that the combination of rhenium oxide and magnesium oxide resulted in extremely poor olefin production of both ethylene and propylene. Most of the material was converted to carbon oxides and hydrogen. Manganese oxide on a calcium oxide base resulted in lower selectivity to olefins than the quartz chips (thermal) and increased production of ethane.

An attempt was also made to utilize manganese oxide on a barium oxide base. However, it appeared that the formation of carbon dioxide during the reaction converted the barium to barium carbonate, which melted into a solid mass which was completely ineffective.

Even when steam is co-fed to the process, as in the previous examples, thereby extending the effective life of the catalyst, regeneration was found to be necessary about every ten minutes in order to maintain the selectivity to ethylene production. As a practical matter and for comparative purposes, the catalyst is considered to be ineffective or inactive and to require regeneration when the selectivity to ethylene falls to a value essentially equal to the selectivity to propylene.

In accordance with a further aspect of the present invention, it has been found that small or promoting amounts of at least one oxide of at least one metal selected from the group consisting of calcium, barium, strontium, tin and antimony, when added to the manganese oxide/magnesium oxide catalyst, not only greatly extend the life or effectiveness of the manganese oxide/magnesium oxide catalyst but also improve the selectivity to $C_2$'s and particularly ethylene.

EXAMPLE 4

Comparisons were made of manganese oxide/magnesium oxide catalyst containing small amounts of the subject promotors in their oxide form (again expressed as elemental metal based on the total catalyst weight), with Group IA metals on the manganese oxide/magnesium oxide catalyst, quartz chips and the manganese oxide/magnesium oxide without promoter. This series of tests was carried out in the same manner as the previous example and under the same conditions except that the temperature is maintained substantially constant and thus the conversion varied.

TABLE 4

| Promoter, wt. % | Bed Temp, °C. | Conv. | $C_2=$ | $C_3=$ | $C_2$ | $C_2= + C_3= + C_2$ | $\dfrac{C_2= + C_2}{C_3}$ |
|---|---|---|---|---|---|---|---|
| Quartz Chips only | 700 | 42 | 30 | 40 | 6 | 76.0 | 0.9 |
| 4% Mn/MgO only | 659 | 50 | 35.0 | 27.0 | 19.0 | 81.0 | 2.00 |
| 3% Ca | 703 | 78.4 | 35.1 | 22.1 | 15.0 | 72.2 | 2.3 |
| 1% Li | 706 | 67.3 | 31.4 | 35.0 | 7.5 | 73.9 | 1.1 |
| 1% Na | 704 | 76.5 | 27.2 | 35.1 | 8.8 | 71.1 | 1.0 |
| 1% K | 710 | 90.1 | 25.8 | 28.8 | 12.1 | 66.7 | 1.3 |
| 1% Ba | 706 | 72.0 | 32.5 | 27.5 | 10.4 | 70.4 | 1.6 |
| 2% Sn | 707 | 84.0 | 33.0 | 22.2 | 11.0 | 66.2 | 2.0 |
| 2% Sb | 708 | 83.5 | 32.4 | 23.9 | 10.9 | 67.2 | 1.8 |

It is to be observed from Table 4 that the use of Group IA metals as promoters resulted in little or no improvement over the thermal converson (quartz chips), either in selectivity to $C_2$'s or ethylene. Of the above specified promoters, at least one oxide of at least one metal selected from the group consisting of calcium, barium and strontium is preferred. However, the most effective and most desirable promoter is calcium, as will be illustrated from the following examples.

In the following examples catalysts comprising a combination of calcium oxide, manganese oxide and magnesium oxide were prepared either by coprecipitation, impregnation or mixing of calcium and magnesium nitrates with magnesium hydroxide in a blender. The catalysts were dried at about 120° C. for about 5 hours, calcined in air at 300° C. (about 3 hours) and then at a temperature of about 775° C. to 800° C. (about 4 hours). Unless otherwise noted, all tests use 25 cc of catalysts, a feed of 100 cc/min of n-butane and 100 cc/min of steam and regeneration with 100 cc/min of air. Sample times were measured from the time the feed was started.

EXAMPLE 5

The greatly improved effective life which can be obtained by adding calcium oxide, as a promoter on the manganese oxide/magnesium catalyst, is illustrated by the following table comparing catalysts containing varying amounts of calcium oxide on manganese oxide/magnesium oxide with manganese oxide/magnesium oxide alone after feed times of four minutes and 90 minutes, respectively. The catalysts were cycled several times between air regeneration and feed before the data of the table were taken and were held at a reactor temperature of 650° C.

TABLE 5

|  | 5% Mn/MgO | 3% Ca/ 5% Mn/MgO | 6% Ca/ 5% Mn/MgO |
|---|---|---|---|
| 4 min sample |  |  |  |
| Conversion | 38.6 | 38.2 | 31.5 |
| Selectivity |  |  |  |
| $C_2=$ | 36.7 | 33.9 | 34.4 |
| $C_3=$ | 23.4 | 26.2 | 28.9 |
| $C_2$ | 23.4 | 20.9 | 19.1 |
| $C_3$ | 0.3 | 0.4 | 0.4 |
| $C_4= + C_4= =$ | 4.3 | 3.5 | 3.2 |
| $CH_4$ | 10.4 | 12.2 | 13.1 |
| $CO + CO_2$ | 1.5 | 2.9 | 0.9 |
| 90 min sample |  |  |  |
| Conversion | 22.7 | 30.0 | 32.2 |
| Selectivity |  |  |  |
| $C_2=$ | 32.2 | 33.9 | 33.4 |
| $C_3=$ | 27.5 | 27.5 | 29.3 |
| $C_2$ | 14.4 | 17.9 | 16.3 |
| $C_3$ | 0.5 | 0.3 | 0.4 |
| $C_4= + C_4= =$ | 10.3 | 4.2 | 3.6 |
| $CH_4$ | 13.3 | 12.7 | 13.8 |
| $CO + CO_2$ | 2.0 | 3.4 | 3.2 |

As is obvious from the above, the catalyst promoted with calcium maintains its selectivity to $C_2$'s and ethylene for a longer period of time and conversion does not decrease as rapidly with the promoted catalyst.

Based upon the above and other experimental evidence, the amounts of promoter, particularly calcium, which are effective are between about 1 and about 15 wt. % (wt. % of elemental calcium based on the total catalyst weight) with the preferred range being between about 2 and about 6 wt. %.

EXAMPLE 6

A further series of experiments was carried out utilizing a catalyst containing 3 wt. % calcium (expressed in terms of elemental calcium based on the total weight of the catalyst) in its oxide form, together with varying amounts of manganese oxide and a balance of magnesium oxide. All tests were carried out under essentially the same conditions as in the previous examples, except that a bed temperature of 700° C. was maintained. A 1/1 ratio of steam/hydrocarbon (n-butane) was utilized. Quartz chips were used for the thermal cracking comparison.

TABLE 6

| % Mn | Conv. | Selectivity | | | | | | |
|---|---|---|---|---|---|---|---|---|
| | | C= | $C_3^=$ | $C_2$ | $C_3$ | $C_4^=$ + $C_4^=$ = | $CH_4$ | $CO_x$ |
| Thermal | 28 | 28 | 43 | 7 | — | 5 | 17 | 0 |
| 0.1 | 24 | 32 | 37 | 8 | — | 3 | 16 | 1 |
| 0.2 | 32 | 37 | 30 | 14 | — | 3 | 15 | 2 |
| 0.5 | 37 | 42 | 25 | 16 | — | 2 | 11 | 1 |
| 1.0 | 45 | 41 | 21 | 20 | — | 2 | 10 | 2 |
| 4.0 | 47 | 42 | 21 | 20 | — | 2 | 10 | 2 |
| 10.0 | 47 | 42 | 20 | 20 | — | 2 | 10 | 1 |
| 13.0 | 48 | 41 | 21 | 20 | — | 2 | 10 | 2 |
| 18.0 | 46 | 40 | 23 | 19 | — | 2 | 11 | 2 |
| 24.0 | 55 | 40 | 20 | 21 | — | 2 | 12 | 3 |
| 29.0 | 57 | 40 | 21 | 19 | — | 2 | 13 | 4 |

Based on the above, in the combination of promoter/manganese oxide/magnesium oxide, the preferred range of manganese oxide is between about 0.2 and about 10 wt. % (elemental manganese based on the total weight of a catalyst).

A combination of 3% calcium oxide (expressed as elemental calcium)/4% manganese oxide (expressed in terms of elemental manganese)/magnesium oxide was also tested on various feedstocks.

It was found that the subject catalysts made no improvement, in conversion or selectivity, over the thermal (quartz chips) conversion, with an ethane feed.

Utilizing a propane feed at a 1/1 steam/hydrocarbon ratio, the following comparison with thermal conversion was obtained.

TABLE 7

| Catalyst | Temp | Conv. | Selectivity | | | | | | |
|---|---|---|---|---|---|---|---|---|---|
| | | | $C_2^=$ | $C_2$ | $C_3^=$ | $C_4^=$ + $C_4^=$ = | | $C_4$ | $CH_4$ | $CO_x$ |
| Quartz Chips | 717° C. | 30.0 | 34.5 | 3.2 | 42.3 | 1.4 | 0.2 | 18.3 | 0 |
| 3% Ca/4% Mn/MgO | 702 | 50.5 | 46.4 | 2.7 | 20.4 | — | — | 28.0 | 2.3 |

It is to be seen from the above table that results with the subject catalyst show improved conversion and selectivity to ethylene.

A comparative test was also run utilizing a manganese oxide/magnesium oxide catalyst as compared with quartz chips (thermal) to convert isobutane at a 1/1 steam/hydrocarbon ratio.

TABLE 8

| Catalyst | Temp | Conv. | Selectivity | | | | | | |
|---|---|---|---|---|---|---|---|---|---|
| | | | $C_2^=$ | $C_3^=$ | $C_2$ | $C_3$ | $iC_4^=$ | $CH_4$ | $CO_x$ |
| Quartz Chips | 700° C. | 48 | 6 | 33 | 1 | 1 | 46 | 14 | — |
| 8% Mn/MgO | 700 | 60 | 7 | 42 | 2 | 1 | 22 | 24 | 2 |

It is to be observed from the above that the subject catalyst shifts the product significantly from isobutene to propylene and ethylene, when compared with thermal conversion (quartz chips).

The effects of gas hourly space velocity (GHSV) where also studied, it was found, in this respect, that conversion of feed hydrocarbons decreases as the space velocity goes up.

It has further been discovered, in accordance with the present invention that the presence of "bound" or "fixed" sulfur in the components used to prepare the catalyst can be detrimental, to the extent that it tends to inhibit selectivity of the catalyst for the production of $C_2$'s. Such sulfur is referred to as "bound" or "fixed" sulfur, since it does not appear to be converted to $H_2S$ or otherwise lost during the hydrocarbon conversion process or the regeneration step and is probably present in sulfate form.

EXAMPLE 9

The effect of bound or fixed sulfur in the catalyst is illustrated by the following series of runs, which were conducted utilizing a catalyst comprising 3% calcium/5% manganese/magnesium oxide for the cracking of n-butane at a 1/1 steam/hydrocarbon ratio and at a conversion of 50%. Other conditions and the mode of operation are the same as those previously utilized in the examples. The specific catalysts were made from magnesium oxides obtained from various sources and containing differing amounts of bound or fixed sulfur.

TABLE 9

| Catalyst No. | 1 | 2 | 3 | 4 | 5 | 6 |
|---|---|---|---|---|---|---|
| S in MgO Base, Wt. % | 0.41 | 0.14 | 0.09 | 0.25 | 0.07 | 0.21 |
| Selectivity, % | | | | | | |
| $C_2^=$ | 34 | 34 | 36 | 35 | 36 | 31 |
| $C_3^=$ | 25 | 28 | 24 | 29 | 26 | 30 |
| $C_2$ | 18 | 18 | 25 | 17 | 21 | 19 |
| $C_4^=$ | 4 | 3 | 3 | 3 | 2 | 4 |
| $C_2^=$ + $C_2$ | 52 | 52 | 61 | 52 | 57 | 50 |

It is apparent from the above that catalysts with low bound or fixed sulfur levels, such as catalysts 3 and 5, resulted in the highest total selectivities to the desirable $C_2$ products. Accordingly, it is highly desirable that catalyst components having low bound or fixed sulfur contents be selected or that the sulfur compounds be removed from the catalyst components, by methods known to those skilled in the art, before utilization and preparation of the catalysts. In general, the total sulfur content of the catalyst, expressed in terms of elemental sulfur based on the total weight of the catalyst, should be less than about 0.2 wt. % and preferably less than about 0.1 wt. %. Usually, these low concentrations of sulfur can be attained by selecting appropriate major components such as the base component or removing the sulfur from the major components or the base component. recognized that these and other specific recitals are for illustrative purposes and to set forth the best mode only and are not to be considered limiting.

That which is claimed:

1. A method for the conversion of feed hydrocarbons comprising at least one of $C_3$ and $C_4$ hydrocarbons to $C_2$ product hydrocarbons, comprising:
    contacting said feed hydrocarbons with a contact material, consisting essentially of:

(a) about 0.1 to 30 wt. % of at least one oxide of manganese, and (b) the balance of at least one oxide of magnesium, said wt. % being expressed in terms of the element based on the total weight of the contact material, under conditions sufficient to selectively convert said feed hydrocarbons to said $C_2$ product hydrocarbons including: a temperature between about 625° C. and about 850° C.

2. A method in accordance with claim 1 wherein the feed hydrocarbons comprise propane.

3. A method in accordance with claim 1 wherein the feed hydrocarbons comprise butanes.

4. A method in accordance with claim 1 wherein the feed hydrocarbons comprise a mixture of propane and butanes.

5. A method in accordance with claim 1 wherein the catalyst contains less than about 0.2 wt. % sulfur, expressed in terms of elemental sulfur based on the total weight of said catalyst.

6. A method in accordance with 1 wherein the conditions are sufficient to selectively convert the feed hydrocarbons to ethylene.

7. A method in accordance with claim 1 wherein the method is carried out in the presence of steam.

8. A method in accordance with claim 7 wherein the mole ratio of steam/feed hydrocarbons is less than about 10/1.

9. A method in accordance with claim 8 wherein the mole ratio of steam/feed hydrocarbons is between about 0.5/1 and 5/1.

10. A method in accordance with claim 1 wherein the method is carried out in the presence of steam.

11. A method in accordance with claim 10 wherein the mole ratio of steam/feed hydrocarbons is less than about 10/1.

12. A method in accordance with claim 11 wherein the mole ratio of steam/feed hydrocarbons is between about 0.5/1 and about 5/1.

13. A method for the conversion of feed hydrocarbons comprising at least one of $C_3$ and $C_4$ hydrocarbons to $C_2$ product hydrocarbons, comprising:
contacting said feed hydrocarbons with a contact material, consisting of:

(a) about 0.1 to 30 wt. % of at least one oxide of manganese, (b) about 1 to 15 wt. % of at least one oxide of at least one metal selected from the group consisting of calcium, barium, strontium, tin and antimony, and (c) the balance of at least one oxide of magnesium, said wt. % being expressed in terms of the element based on the total weight of the contact material, under conditions sufficient to selectively convert said feed hydrocarbons to said $C_2$ product hydrocarbons, including: a temperature between about 625° C. and about 850° C.

14. A method in accordance with claim 13 wherein the feed hydrocarbons comprise propane.

15. A method in accordance with claim 13 wherein the feed hydrocarbons comprise butanes.

16. A method in accordance with claim 13 wherein the feed hydrocarbons comprise a mixture of propane and butanes.

17. A method in accordance with claim 13 wherein at least one oxide of calcium is present.

18. A method in accordance with claim 13 wherein the catalyst contains less than about 0.2 wt. % sulfur, expressed in terms of elemental sulfur based on the total weight of said catalyst.

19. A method in accordance with claim 13 wherein the conditions are sufficient to selectively convert the feed hydrocarbons to ethylene.

* * * * *